US007824344B1

(12) United States Patent
Altschul

(10) Patent No.: US 7,824,344 B1
(45) Date of Patent: Nov. 2, 2010

(54) METHOD AND APPARATUS FOR NON-INVASIVE ANALYSIS OF SALIVA

(75) Inventor: Randice Lisa Altschul, Cliffside Park, NJ (US)

(73) Assignee: Pop Test LLC, Cliffside Park, NJ (US)

( * ) Notice: Subject to any disclaimer, the term of this patent is extended or adjusted under 35 U.S.C. 154(b) by 0 days.

(21) Appl. No.: 12/218,950

(22) Filed: Jul. 18, 2008

Related U.S. Application Data

(60) Provisional application No. 60/951,298, filed on Jul. 23, 2007.

(51) Int. Cl.
*A61B 5/00* (2006.01)
*B65D 81/00* (2006.01)
*G01N 21/00* (2006.01)
*G01N 31/22* (2006.01)

(52) U.S. Cl. .................. 600/573; 600/584; 422/58; 422/61; 435/805; 435/810

(58) Field of Classification Search .............. 600/573, 600/580, 584, 582; 422/56–58, 61; 435/287.7, 435/287.8, 287.9, 805, 810, 969, 970, 975; 436/63–71, 808, 810, 823; 206/305, 459.1, 206/459.5, 804, 820, 828
See application file for complete search history.

(56) References Cited

U.S. PATENT DOCUMENTS

| 1,967,557 | A | * | 7/1934 | John ........................ 422/56 |
| 5,182,191 | A | * | 1/1993 | Fan et al. ................. 435/7.9 |
| 5,306,623 | A | * | 4/1994 | Kiser et al. ................ 435/14 |
| 5,320,217 | A | * | 6/1994 | Lenarz ..................... 206/209 |
| 5,413,761 | A | * | 5/1995 | Dulaney .................... 422/56 |
| 5,747,351 | A | * | 5/1998 | Hemmati ................... 436/514 |
| 5,910,122 | A | * | 6/1999 | D'Angelo .................. 600/573 |
| 6,010,910 | A | * | 1/2000 | Radcliffe et al. ............ 436/63 |
| 6,102,872 | A | * | 8/2000 | Doneen et al. ............. 600/582 |
| 6,326,214 | B1 | * | 12/2001 | Liu et al. ................... 436/518 |
| 7,597,849 | B2 | * | 10/2009 | Sangha ...................... 422/99 |
| 2002/0127143 | A1 | * | 9/2002 | Kuo ......................... 422/68.1 |
| 2005/0250218 | A1 | * | 11/2005 | Andrelczyk et al. ......... 436/169 |

* cited by examiner

*Primary Examiner*—Max Hindenburg
*Assistant Examiner*—H. Q. Nguyen
(74) *Attorney, Agent, or Firm*—Arthur Jacob

(57) ABSTRACT

A method and apparatus for non-invasive analysis of saliva includes a user friendly lolli-pop like apparatus that is self contained and provides the user with a method to stimulate saliva by sucking on the pop head. The saliva activates a color change reaction on the apparatus that results in a visual response that can be compared to a user gauge for analysis in monitoring health conditions and concerns.

13 Claims, 6 Drawing Sheets

METHOD AND APPARATUS FOR NON-INVASIVE ANALYSIS OF SALIVA

This application claims the priority date of Provisional Application No. 60/951,298 filed Jul. 23, 2007, the substance of which is incorporated herein by reference thereto.

The present invention relates generally to the analysis of saliva through a user friendly lolli-pop like apparatus and pertains, more specifically, to a non-invasive apparatus to stimulate saliva and result in a color change reaction on the pop, filtered stick or holding chamber.

The need for self monitoring for a variety of ailments and conditions has grown exponentially over the years. With testing needs ranging from diabetes glucose levels, to alcohol levels to pregnancy, etc. The near epidemic rise in diabetes throughout the World has resulted in a need for a less invasive means of testing glucose levels. Today's methods for testing and monitoring most often result in the user having to provide blood samples to monitor one's condition. As such, the present invention provides several objects and advantages, some of which are summarized as follows: Provides a user friendly non-invasive mode for testing which allows the use of a less expensive apparatus suitable for more widespread use and acceptance; enables greater convenience in carrying about and use in testing; allows greater convenience in purchasing; provides a simplified visual mode for monitoring test results; reduces potential hazards of incorrect evaluation of results; enables the economical manufacture and distribution of relatively low-cost, reliable diagnostic test apparatus, thereby opening new and larger markets for testing apparatus.

The above objects and advantages, as well as further objects and advantages, are attained by the present invention which may be described briefly as a non-invasive testing apparatus for monitoring of glucose concentration; pregnancy; alcohol levels; keto levels; or various drug presence. The apparatus comprising: a means for saliva stimulation; a candy like component that may or may not be sugar based; a means for color change activation; a filtration to eliminate impurities and a gauge for visual comparison of the results.

The invention will be understood more fully, while still further objects and advantages will become apparent, in the following detailed description of preferred embodiments of the invention in the accompanying drawings, in which.

Figure 1:
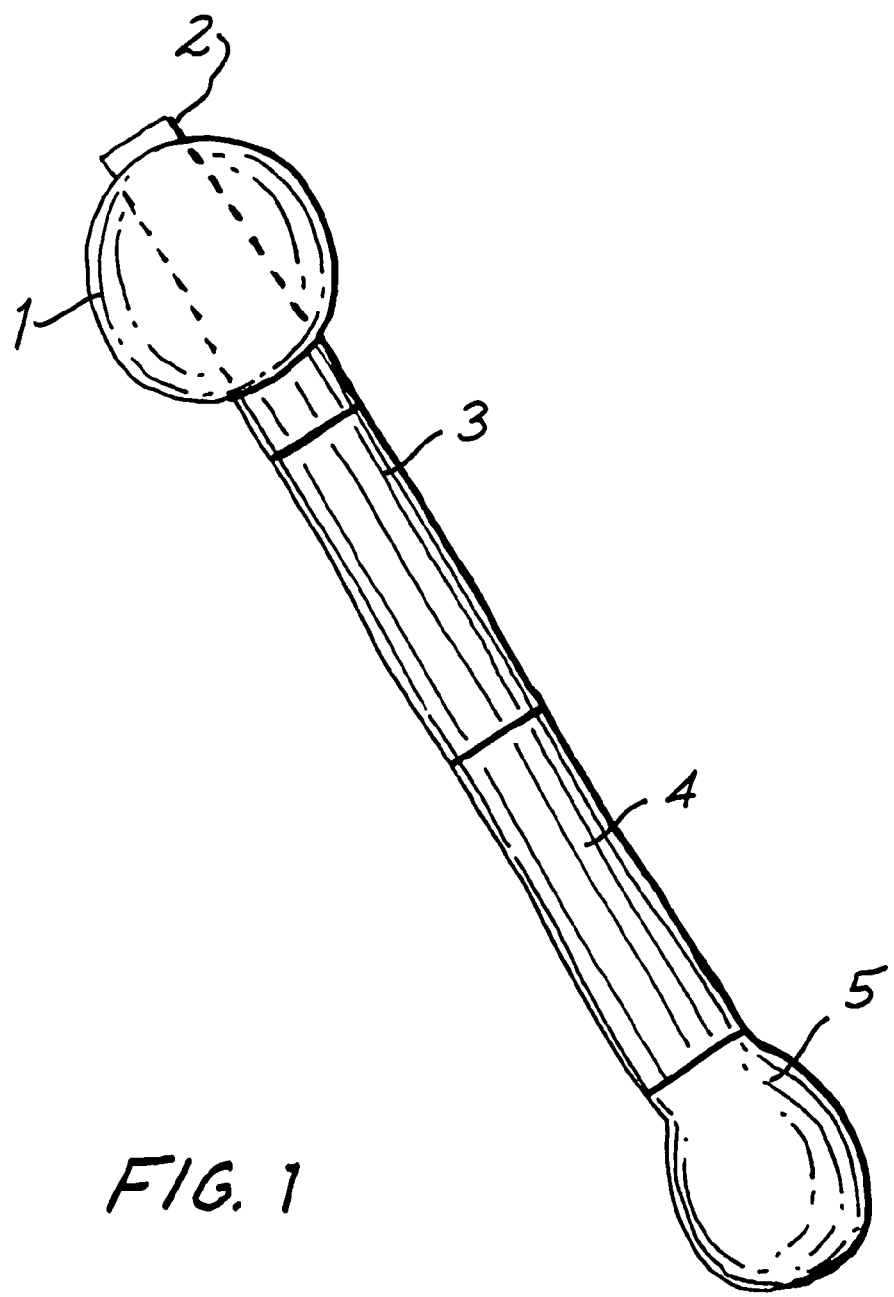
FIG. 1 is a detailed pictorial view of the present invention showing the various embodiments that the testing apparatus can comprise including but not limited to, the head, the stem, the base.

Referring now to the drawing and especially to FIG. 1 thereof, an apparatus for non-invasive analysis of saliva constructed in accordance with the present invention is shown. This embodiment includes a lolli-pop like head 1, saliva stem 2, absorbent filter 3, saliva holding chamber 4 and is activated by squeezing suction ball at bottom of stem 5. The user holds the apparatus sucks on the pop head 1, squeezes the suction ball 5, saliva enters the top opening 2, flows through the filter 3 and is housed for color change results in 4.

Figure 2:
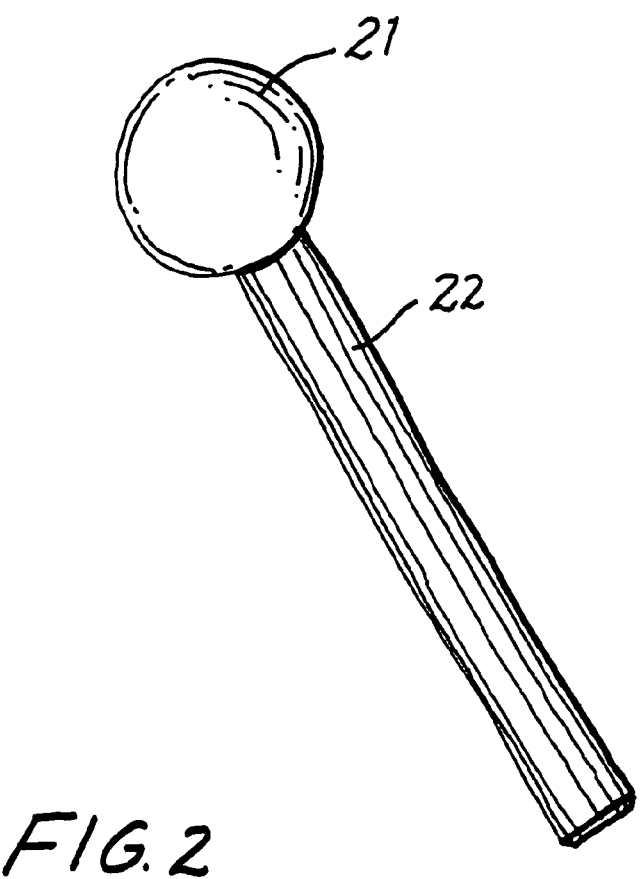
FIG. 2 is a pictorial view showing the testing apparatus with fewer components.
Figure 3:
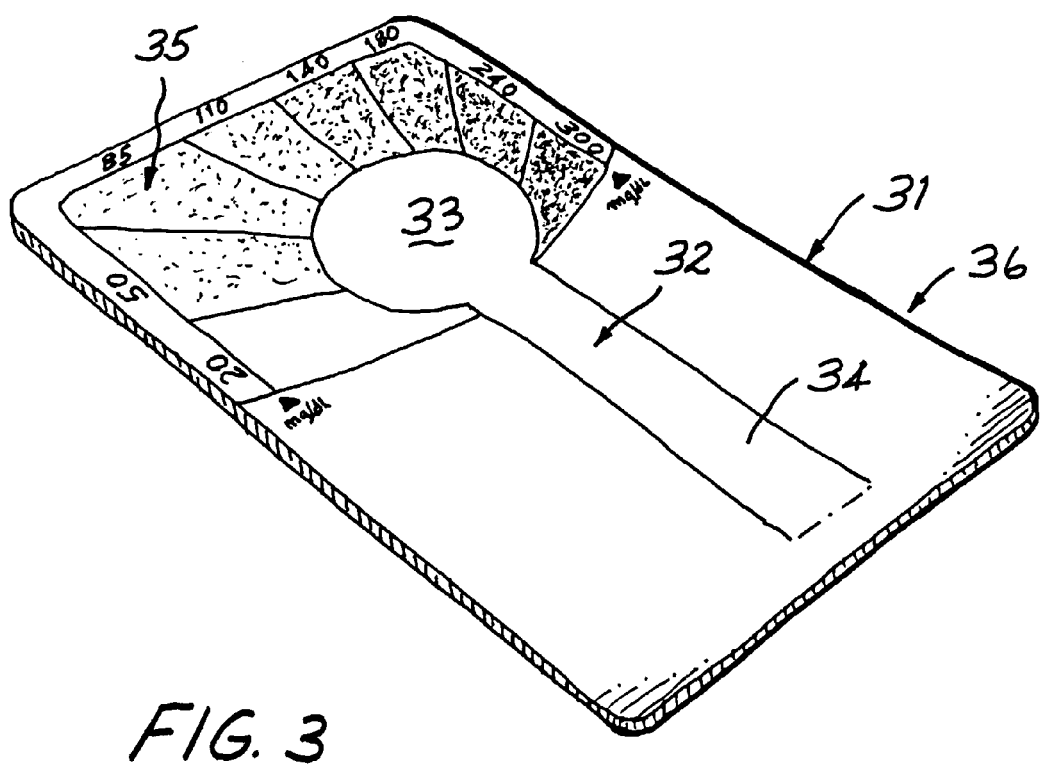
FIG. 3 is a pictorial view showing a compact non-invasive apparatus for the analysis of saliva constructed in accordance with the present invention.
Figure 4:
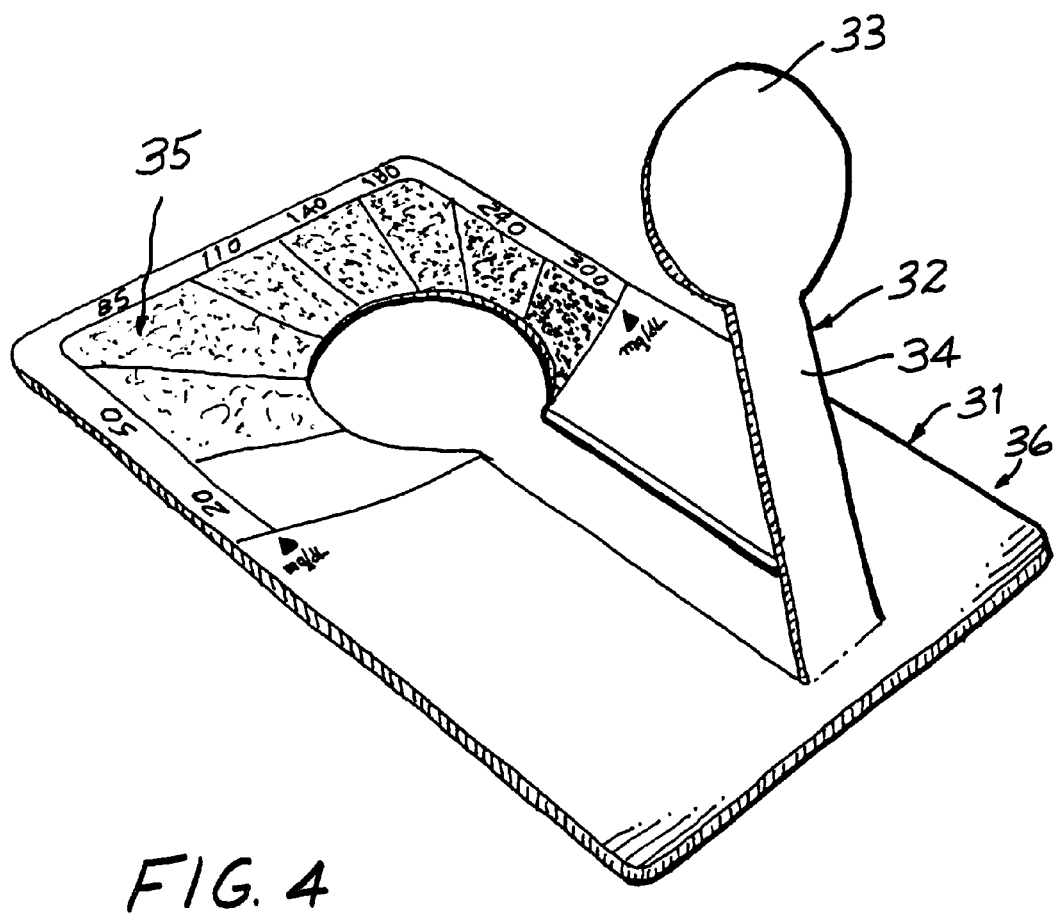
FIG. 4 is a pictorial view showing the method of the apparatus for use as a lolli-pop like test.
Figure 5:
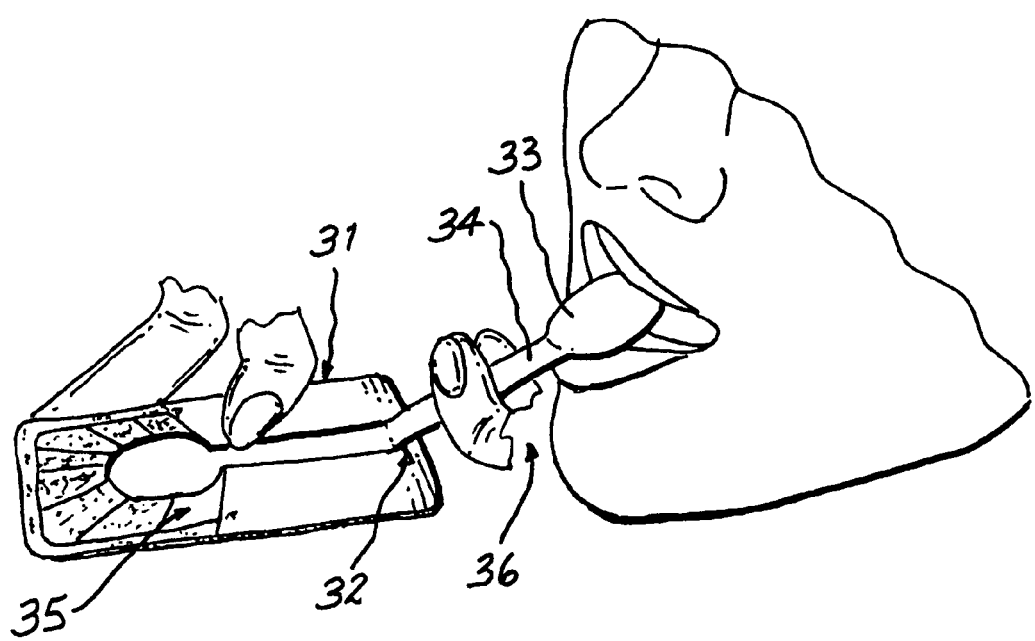
FIG. 5 is a pictorial view showing the method of use of the apparatus.
Figure 6:
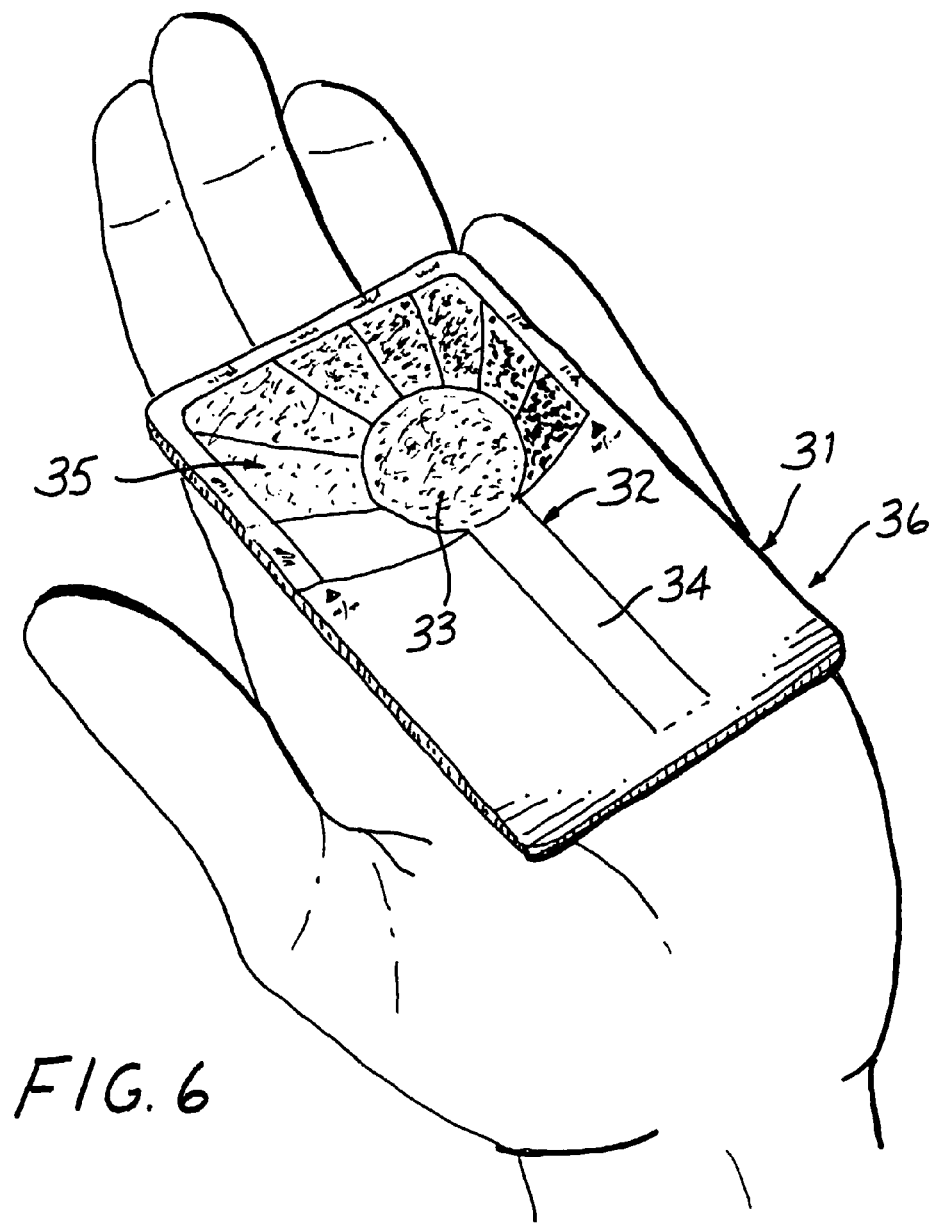
FIG. 6 is a pictorial view showing the results of the saliva test.

Referring now to the drawing and especially FIG. 2 thereof, an apparatus for non-invasive analysis of saliva constructed in accordance with the present invention is shown. This embodiment includes a lolli-pop like head 21 and a stem 22. The user holds the stem 22, sucks on the lolli-pop head 21, saliva is stimulated and the head 21 changes color.

Turning now to FIGS. 3 through 6, thereof, an apparatus for non-invasive analysis of saliva constructed in accordance with the present invention is shown. This embodiment shows the present invention in a card form with built-in gauge for monitoring results of the test therein.

Self contained apparatus 31, bend out Lolli-pop 32, pop head 33, stem 34, gauge 35, method of use 36. The user takes the card 31, his method of use 36 is to bend out the lolli-pop apparatus 32, holds onto the stem 34, sucks on the lolli-pop head 33, saliva is stimulated resulting in a color change to head 33, the stem 34 is bent back in place, the pop head 33 color results, is compared to the gauge 35 for analysis.

The present invention provides a very compact and practical arrangement for analysis of saliva for health conditions. It will be seen that the present invention attains all of the objects and advantages summarized above, namely: Provides a method for monitoring and analysis of saliva which allows the use of a non-invasive low cost apparatus suitable for more widespread use and acceptance; enables greater convenience in monitoring health concerns; allows greater convenience in purchasing and using analysis apparatus; reduces potential hazards associated with incorrect results of saliva analysis; provides greater versatility in the design and function of analysis apparatus; enables the economical manufacture and distribution of low cost, reliable analysis apparatus, thereby opening up new and larger markets for analysis of saliva.

It is understood that the above detailed description of preferred embodiments of the invention is provided by way of example only. Various details of design and construction may be modified without departing from the true spirit and scope of the invention, as set forth in the appended claims.

The embodiments of the invention in which an exclusive property or privilege is claimed are defined as follows:

1. A self-contained apparatus for conducting a non-invasive analysis of saliva to determine a level of a certain constituent present in the saliva, the apparatus comprising:

a flat card-like device having a flat configuration resembling a relatively thin card;

a head having a lolli-pop-like configuration for receiving on the head saliva from a user;

a means on the head capable of reacting with the certain constituent to display a visible color change to the head indicative of a level of the certain constituent in the saliva received on the head;

a stem connected to the head to provide the user with a simple means to hold the apparatus; and a gauge including visible areas of color representing different levels of the certain constituent, the areas of color being displayed on the card-like device, placed relative to the head and the stem for enabling juxtaposition of the head with the gauge for a visual comparison of the color change at the head with the areas of color of the gauge, thereby providing a direct visual determination of the level of the certain constituent in the saliva received on the head, the head and the stem being die-cut within the card-like device so that the stem is pivoted out of the flat configuration for placement of the head in juxtaposition with a user's mouth to facilitate reception of the saliva on the head, and is pivoted subsequently back into the card-like device to insert the head within the card-like device confined in side-by-side contiguity with the gauge to facilitate a direct visual comparison of the color change of the head with the areas of color of the gauge.

2. The invention of claim 1 wherein the certain constituent is associated with pregnancy and the analysis of the saliva is for pregnancy determination.

3. The invention of claim 1 wherein the certain constituent is alcohol and the analysis of the saliva is of alcohol levels.

4. The invention of claim 1 wherein the certain constituent is keto and the analysis of the saliva is of keto levels.

5. The invention of claim 1 wherein the certain constituent is a drug and the analysis of the saliva is for drug presence.

6. The invention of claim 1 wherein the gauge includes specific numbers and ranges of color to reflect the results of the particular saliva analysis.

7. A method for conducting, within a self-contained apparatus, a non-invasive analysis of saliva to determine a level of a certain constituent present in the saliva, the method comprising:

providing a flat card-like device having a flat configuration resembling a relatively thin card;

providing a head die-cut within the card-like device, the head having a lolli-pop-like configuration and a means capable of reacting with the certain constituent for displaying a visible color change to the head indicative of a level of the certain constituent in the saliva;

providing a stem die-cut within the card-like device and connected to the head to provide the user with a simple means to hold the apparatus;

providing a gauge having visible areas of color representing different levels of the certain constituent, the areas of color being displayed on the card-like device, such that the stem enables selective movement of the head between a first position wherein the head is lifted out of the card-like device by pivoting the stem away from the gauge, and a second position wherein the head is inserted back into the card-like device by pivoting the stem so that the head is confined in side-by-side contiguity with the gauge;

pivoting the stem to place the head in the first position and, with the head in the first position, placing the head in juxtaposition with a user's mouth for receiving saliva on the head from the user;

subsequently pivoting the stem to move the head into the second position to confine the head within the card-like device in side-by-side contiguity with the gauge; and conducting a direct visual comparison of the color change to the head with the areas of color of the gauge within the self-contained apparatus.

8. The invention of claim 7 wherein the certain constituent is associated with pregnancy and the analysis of the saliva is for pregnancy determination.

9. The invention of claim 7 wherein the certain constituent is alcohol and the analysis of the saliva is of alcohol levels.

10. The invention of claim 7 wherein the certain constituent is keto and the analysis of the saliva is of keto levels.

11. The invention of claim 7 wherein the certain constituent is a drug and the analysis of the saliva is for drug presence.

12. The invention of claim 1 wherein the certain constituent is glucose and the analysis of the saliva is of glucose levels.

13. The invention of claim 7 wherein the certain constituent is glucose and the analysis of the saliva is of glucose levels.

\* \* \* \* \*